US009693437B2

(12) United States Patent
Simmons et al.

(10) Patent No.: US 9,693,437 B2
(45) Date of Patent: Jun. 27, 2017

(54) SYSTEMS AND METHODS FOR CONTROLLING X-RAY IMAGING SYSTEMS

(75) Inventors: John Matthew Simmons, Salt Lake City, UT (US); David Barker, Salt Lake City, UT (US); Samuel Alder, Salt Lake City, UT (US); Bret Nicholson, Salt Lake City, UT (US); Robert Bruce Spratt, Jr., Salt Lake City, UT (US)

(73) Assignee: General Electric Company, Schenectady, NY (US)

( * ) Notice: Subject to any disclaimer, the term of this patent is extended or adjusted under 35 U.S.C. 154(b) by 666 days.

(21) Appl. No.: 13/446,176

(22) Filed: Apr. 13, 2012

(65) Prior Publication Data

US 2013/0272499 A1 Oct. 17, 2013

(51) Int. Cl.
*A61B 6/00* (2006.01)
*H05G 1/02* (2006.01)
*G01N 23/04* (2006.01)

(52) U.S. Cl.
CPC .............. *H05G 1/02* (2013.01); *A61B 6/4405* (2013.01); *A61B 6/4441* (2013.01); *A61B 6/467* (2013.01); *A61B 6/487* (2013.01); *A61B 6/548* (2013.01); *G01N 23/04* (2013.01)

(58) Field of Classification Search
CPC .................................................. A61B 6/4441
USPC ................................................. 378/197, 198
See application file for complete search history.

(56) References Cited

U.S. PATENT DOCUMENTS 3,456,114 A 7/1969 Gray
3,456,117 A * 7/1969 Lavery et al. ................ 250/569
4,104,525 A 8/1978 Franke
4,209,706 A * 6/1980 Nunan ........................... 378/189
4,856,036 A 8/1989 Malcolm et al.
5,077,771 A 12/1991 Skillicorn et al.
5,627,873 A 5/1997 Hanover et al.
5,631,943 A 5/1997 Miles
(Continued)

FOREIGN PATENT DOCUMENTS

CN 1654012 A 8/2005
CN 101212931 A 7/2008
(Continued)

OTHER PUBLICATIONS

Unofficial English translation of Chinese Office Action and Search Report issued in connection with corresponding CN Application No. 201310125963.X on Feb. 14, 2016.

*Primary Examiner* — David J Makiya
*Assistant Examiner* — Dani Fox (57) ABSTRACT

Systems and methods for controlling an X-ray imaging system are described. The systems and methods typically include a support arm with a first end and a second end. The first end of the support arm connects to an articulating arm assembly and the second end of the support arm pivotally attaches to an X-ray imaging arm at a pivot joint so that the pivot joint functions as an axis of orbital rotation for the X-ray imaging arm. One or more controls for the X-ray imaging system are disposed on the support arm for the X-ray imaging arm. The controls can therefore remain stationary while the X-ray imaging arm rotates orbitally. The support arm can include a single member or a double member and one or more controls can be disposed on each member of the support arm. Other embodiments are also described.

4 Claims, 7 Drawing Sheets

(56) References Cited

U.S. PATENT DOCUMENTS

| | | | |
|---|---|---|---|
| 5,642,395 A * | 6/1997 | Anderton | A61B 6/4225 378/197 |
| 6,007,243 A | 12/1999 | Ergun et al. | |
| 6,234,672 B1 | 5/2001 | Tomasetti et al. | |
| 6,236,712 B1 | 5/2001 | Tomasetti et al. | |
| 6,256,374 B1 | 7/2001 | Tomasetti et al. | |
| 7,129,666 B2 | 10/2006 | Bauer et al. | |
| 7,591,587 B2 | 9/2009 | Gotoh | |
| 2007/0133753 A1* | 6/2007 | Jakob et al. | 378/198 |
| 2008/0020332 A1* | 1/2008 | Lavenda et al. | 430/495.1 |
| 2009/0046068 A1* | 2/2009 | Griffin | 345/173 |
| 2010/0239073 A1 | 9/2010 | Eaves | |
| 2013/0044409 A1* | 2/2013 | Pegg | 361/679.01 |

FOREIGN PATENT DOCUMENTS

| CN | 101254113 A | 9/2008 |
|---|---|---|
| CN | 201861656 U | 6/2011 |

\* cited by examiner

SYSTEMS AND METHODS FOR CONTROLLING X-RAY IMAGING SYSTEMS

FIELD

This application relates generally to X-ray equipment. More specifically, this application relates to systems and methods for controlling X-ray equipment through the use of one or more controls that are disposed on a support arm of the X-ray equipment.

BACKGROUND

A typical X-ray imaging system comprises an X-ray source and an X-ray detector. X-rays emitted from the X-ray source can impinge on the X-ray detector and provide an X-ray image of an object or subject that is placed between the X-ray source and the detector. In one type of X-ray imaging system, a fluoroscopic imaging system, the X-ray detector is often an image intensifier or, more recently, a flat panel digital detector.

Fluoroscopic imaging systems can be either fixed or mobile. For instance, fixed fluoroscopic imaging systems often include a gantry that is secured to a floor, wall, or ceiling. Additionally, mobile fluoroscopic imaging systems are movable so that they can be used in a variety of clinical environments, such as radiology and surgery departments of a medical facility. The mobile fluoroscopic imaging systems may include a C-arm, G-arm, O-arm, L-arm, or another imaging arm or gantry assembly. A mobile fluoroscopic imaging system may also be configured as a mini C-arm.

In some configurations, a C-arm assembly of a fluoroscopic imaging system remains stationary relative to a subject for single angle imaging. In other configurations, however, the C-arm assembly moves relative to the subject in order to acquire images from multiple angles. In some arrangements, the C-arm assembly is manually repositioned to generate images from different angles while in other arrangements the C-arm assembly is moved along a predetermined path by operation of a motorized drive mechanism in order to generate images from multiple angles.

SUMMARY

This application relates generally to X-ray imaging systems. In particular, this application relates to systems and methods for controlling an X-ray imaging system. The systems and methods typically include a support arm with a first end and a second end. The first end of the support arm connects to an articulating arm assembly and the second end of the support arm pivotally attaches to an X-ray imaging arm at a pivot joint so that the pivot joint functions as an axis of orbital rotation for the X-ray imaging arm. One or more controls for the X-ray imaging system are disposed on the support arm for the X-ray imaging arm. The controls can therefore remain stationary while the X-ray imaging arm rotates orbitally. The support arm can include a single member or a double member and one or more controls can be disposed on each member of the support arm.

BRIEF DESCRIPTION OF THE DRAWINGS

The following description can be better understood in light of the Figures, in which.

The Figures illustrate specific aspects of the described systems and methods for controlling an X-ray imaging system. Together with the following description, the Figures demonstrate and explain the principles of the structures, systems, methods, and principles described herein. In the drawings, the thickness and size of components may be exaggerated or otherwise modified for clarity. The same reference numerals in different drawings represent the same element, and thus their descriptions will not be repeated. Furthermore, well-known structures, materials, or operations are not shown or described in detail to avoid obscuring aspects of the described systems and methods.

DETAILED DESCRIPTION

The following description supplies specific details in order to provide a thorough understanding. Nevertheless, the skilled artisan will understand that the described systems and methods for controlling X-ray imaging systems can be implemented and used without employing these specific details. Indeed, the described systems and methods for controlling X-ray imaging systems can be placed into practice by modifying the described systems and methods and can be used in conjunction with any other apparatus and techniques conventionally used in the industry. For example, while the description below focuses on methods for providing and using controls that are disposed on a support arm that is pivotally connected to an X-ray imaging arm (such as a mini C-arm), the controls and support arm can be used with any other type of X-ray imaging system in which an X-ray imaging arm can pivot in an orbital fashion around a pivot joint attached to the imaging arm. Some examples of such X-ray imaging arms include a standard C-arm, a compact style C-arm, a mini C-arm, a G-arm, an O-arm, an L-arm, and other X-ray imaging arms.

In addition, as the terms on, disposed on, attached to, connected to, or coupled to, etc. are used herein, one object (e.g., a material, element, structure, member, etc.) can be on, disposed on, attached to, connected to, or coupled to another object—regardless of whether the one object is directly on, attached, connected, or coupled to the other object or whether there are one or more intervening objects between the one object and the other object. Also, directions (e.g., on top of, below, above, top, bottom, side, up, down, under, over, upper, lower, lateral, orbital, horizontal, etc.), if provided, are relative and provided solely by way of example and for ease of illustration and discussion and not by way of limitation. Where reference is made to a list of elements (e.g., elements a, b, c), such reference is intended to include any one of the listed elements by itself, any combination of less than all of the listed elements, and/or a combination of all of the listed elements. Furthermore, as used herein, the terms a, an, and one may each be interchangeable with the terms at least one and one or more.

Figure 1:
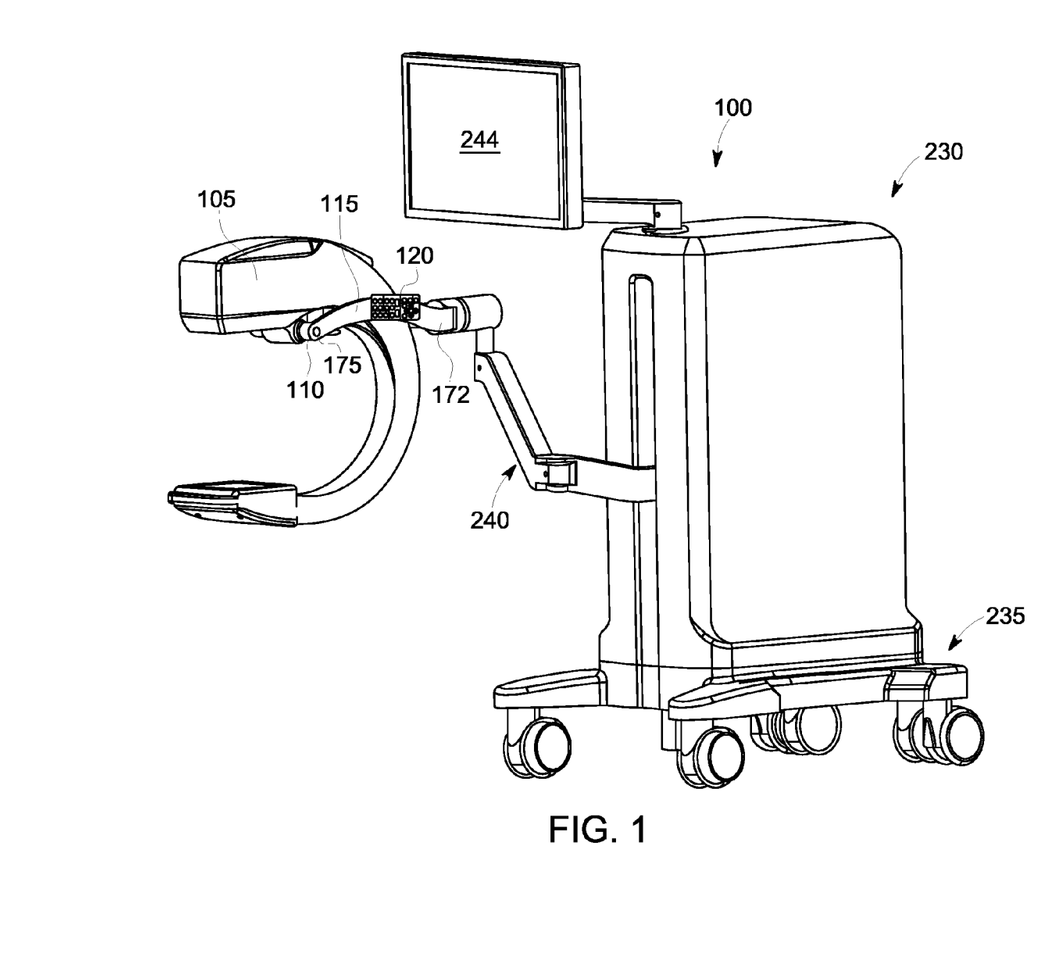
FIG. 1 shows a perspective view of an embodiment of an X-ray imaging system with a control panel disposed on a support arm for an X-ray imaging arm.
Figure 2:
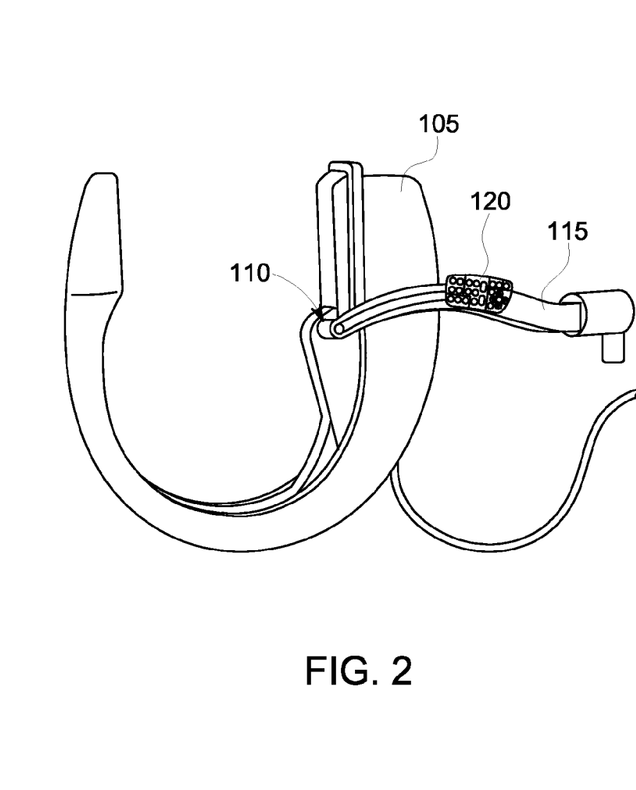
FIG. 2 shows a perspective view of some embodiments of the X-ray imaging arm and the support arm for a wired control panel.
Figure 3:
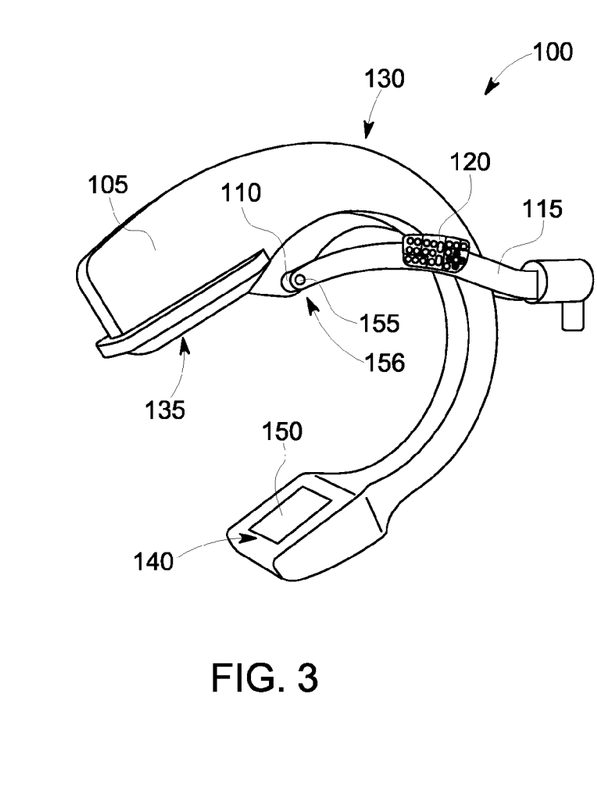
FIG. 3 shows a perspective view of some embodiments of the X-ray imaging arm and support arm for a wireless control panel.

This application relates to systems and methods for controlling X-ray imaging systems using one or more controls that are disposed on a support arm. FIG. 1 shows some embodiments in which the described X-ray imaging system 100 comprises an X-ray imaging arm support structure (e.g., a movable base assembly 230 with a plurality of wheels mounted to the bottom thereof), an articulating arm assembly 240 coupled to the support structure, a support arm assembly 115 having a first end 172 coupled to the articulating arm assembly, an X-ray imaging arm 105 coupled to a second end 175 of the support arm assembly at an orbital pivot joint 110, and a display 244 coupled to the support structure. The support arm assembly 115 includes one or more controls (i.e., X-ray control panels 120) disposed thereon. With such a configuration, the control panel can remain stationary as the imaging arm rotates orbitally. FIGS. 2 and 3 show some embodiments in which the control panel 120 remains stationary on the support arm 115 as the imaging arm 105 rotates orbitally from an under scan position (shown in FIG. 2) to an over scan position (shown in FIG. 3).

The X-ray imaging system 100 can comprise any X-ray imaging arm 105 that allows the system to take X-ray images of any portion of a subject (not shown). In some embodiments, the X-ray imaging arm can comprise a mini C-arm, a compact style C-arm, a standard C-arm, a G-arm, an O-arm, an L-arm, or any other X-ray imaging arm. FIG. 3 shows one configuration in which the X-ray imaging arm 105 is a mini C-arm 130.

In some embodiments, the imaging arm 105 comprises an X-ray source 135, an X-ray detector 140, and all or a portion of the orbital pivot joint 110, as shown in FIG. 3. The imaging arm 105 can comprise any X-ray source 135 and any X-ray detector 140 that allow the X-ray system 100 to take X-ray images. For example, the X-ray source can comprise any source that generates and emits X-rays, including a standard X-ray source, a rotating anode X-ray source, a stationary or fixed anode X-ray source, a solid state X-ray emission source, and/or a fluoroscopic X-ray source. The X-ray detector can comprise any detector that detects X-rays, including an image intensifier and/or a digital flat panel detector 150 (as shown in FIG. 3). The imaging arm 105 can be configured to support the X-ray source 135 and the X-ray detector 140 so that they are respectively disposed at nearly opposite ends of the imaging arm, substantially face each other, and/or can rotate around the orbital pivot joint 110.

The X-ray imaging system 100 can comprise any orbital pivot joint 110 that allows the imaging arm 105 to be pivotally attached to the support arm 115 so that the pivot joint provides an orbital axis of rotation to the imaging arm.

FIG. 3 shows some embodiments in which the orbital pivot joint 110 includes a pivot pin 155, which is attached to the support arm 115 and extends through the imaging arm 105 in a manner that allows the imaging arm to rotate orbitally around the pin. Thus, the imaging arm 105 rotates orbitally about a physical pivot point 156.

Figure 4:
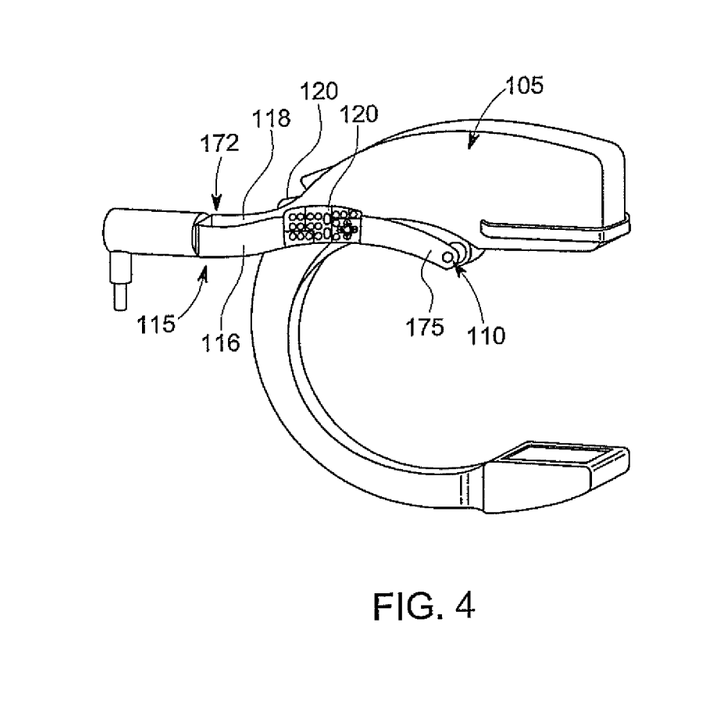
FIG. 4 shows a perspective view of some embodiments of the X-ray imaging arm and a double member support arm with a control panel coupled to each member of the double member support arm.
Figure 5:
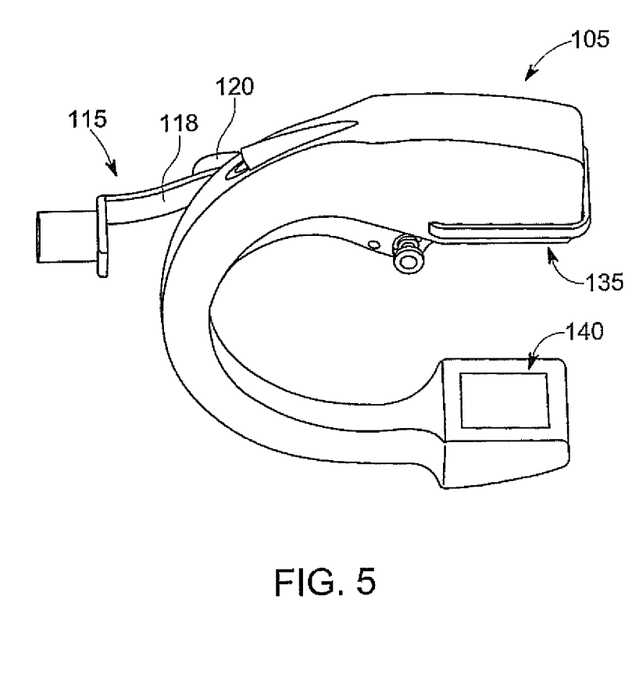
FIG. 5 shows a perspective view of some embodiments of the X-ray imaging arm and a single member support arm with a control panel coupled to the single member support arm.

The X-ray imaging system 100 can comprise a support arm 115. This support arm can be configured to support the imaging arm 105, attach the imaging arm to the articulating arm assembly 240, provide the imaging arm with an axis of orbital rotation, and/or provide the imaging arm with an axis of lateral rotation (e.g., an axis of rotation that is substantially perpendicular to the orbital rotation axis). In some embodiments, the support arm 115 comprises any number of imaging arm support members, including 1, 2, or more. FIG. 4 shows some embodiments in which the support arm 115 (e.g., a double member support arm) comprises a first support member 116 and a second support member 118. FIG. 5 shows other embodiments in which the support arm 115 (e.g., a single member support arm) comprises a single support member 118.

Figure 6:
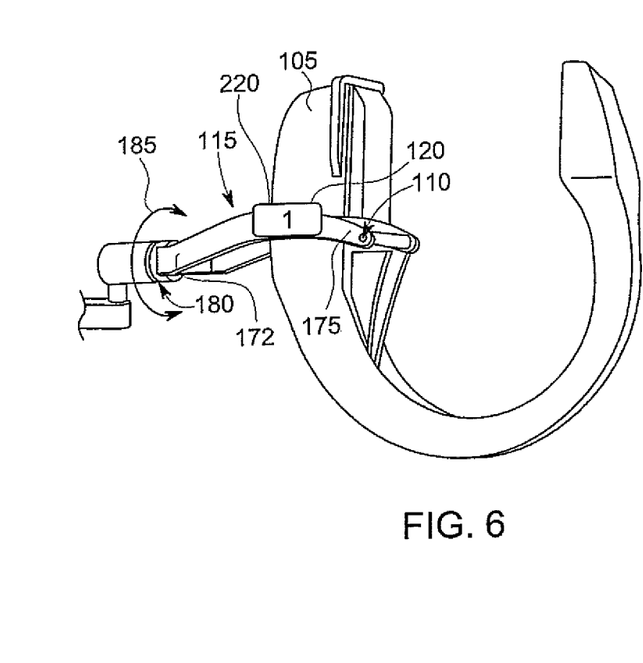
FIG. 6 shows a perspective view of some embodiments of the X-ray imaging arm and the support arm, with the support arm in a first position.
Figure 7:
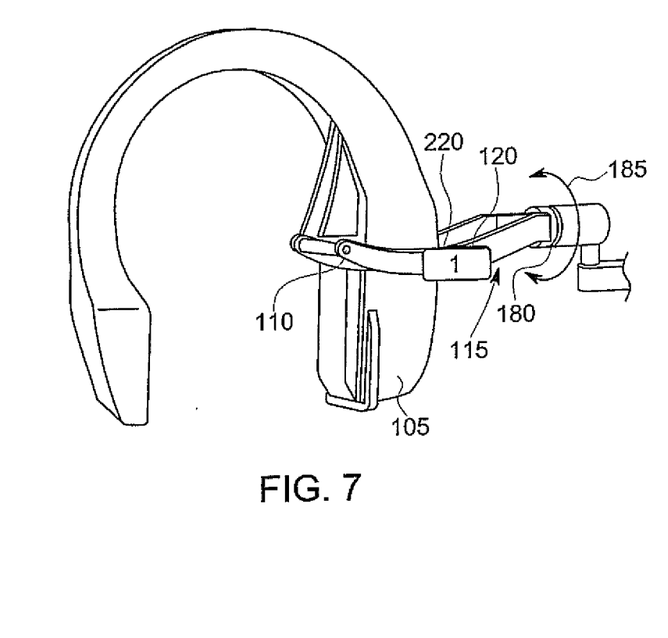
FIG. 7 shows a perspective view of some embodiments of the X-ray imaging arm and the support arm, with the support arm rotated to a second position.

In some configurations, the support arm 115 optionally provides the imaging arm 105 with an axis of lateral rotation. For example, FIG. 6 shows that a first end 172 of the support arm 115 is connected to the orbital pivot joint 110. FIG. 6 also shows that the support arm's second end 175 can be attached to a lateral pivot joint 180, which allows the support arm to rotate clockwise and/or counter-clockwise as indicated by the double pointed arrow 185. FIG. 7 shows some embodiments in which the support arm 115 has been rotated about 180 degrees from the position shown in FIG. 6.

The control panel 120 allows a user to operate one or more functions of the X-ray system 100. The control panel 120 can comprise any type of electrical controls. Some examples of suitable types of controls comprise one or more tactile-membrane switches, toggle switches, buttons, touch-screen interfaces, adjustment knobs, sliding switches, adjustable switches, dome switches, levers, proximity switches, pressure switches, speed switches, temperature switches, tactile switches, relays, momentary switches, motion detection switches, tuners, joysticks, and other switches that can be used to control one or more functions of the X-ray system. In some embodiments, however, the control panel comprises one or more conventional tactile-membrane switches and/or touch-screen interfaces. The control panel can comprise any number of controls, including, 1, 2, 3, 4, 5, 6, 7, 8, 9, 10, or more.

Figure 8:
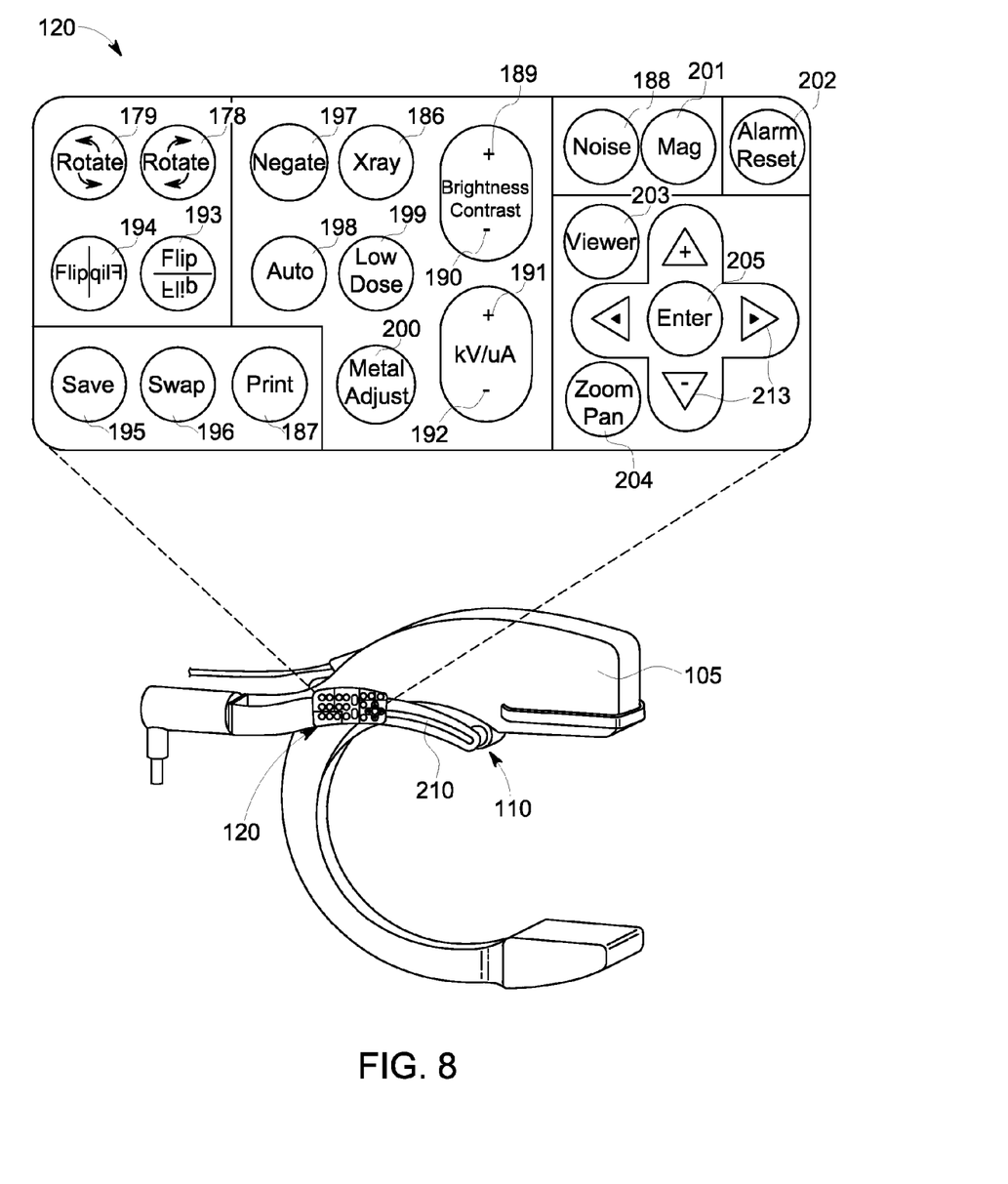
FIG. 8 shows a perspective view of some embodiments of the X-ray imaging arm and the support arm with an enlarged view of an exemplary control panel.

FIG. 8 shows some embodiments of a control panel 120. In these embodiments, the control panel 120 comprises a power switch to turn power on and off to the imaging arm 105. The control panel can also comprise an X-ray activation switch (e.g., X-ray button 186 in FIG. 8) that allows the X-ray source 135 to generate a single X-ray image, multiple images, and/or continuous imaging, on demand. To generate a single image, a user can depress the X-ray control switch twice in rapid succession and then releases the switch so that the X-ray source 135 is activated for a single image or strobe shot. For continuous imaging, the user can depress the X-ray control switch twice in rapid succession and then continue to depress (or hold down) the switch so that the X-ray source is activated and continues to produce X-rays for as long as the switch is depressed to create a real-time, continuous, or cinematic fluoroscopic picture.

The control panel 120 can also comprise a print switch (e.g., print button 187 in FIG. 8) that can be used to cause an X-ray image received from the system 100 to be printed.

The control panel 120 can also comprise a conventional noise suppression switch (e.g., noise button 188 in FIG. 8) that can control the system's noise suppression processing. The noise suppression switch can step the video frame averaging so that each time the switch is depressed, the video noise suppression frame averaging is changed. In some embodiments, each depression of the switch can step the frame averaging from 0 frames to 2, 4, 8, and 16 frames successively, starting with a current frame averaging value and incrementing from there. In such embodiments, when the frame averaging is at 16 and the switch is depressed, the frame averaging value can then roll over to 0 and begin the rotation again.

The control panel 120 can also comprise one or more switches, joy sticks, or other controls that can be used to control one or more servos, pistons, motors, actuators, joints, brakes, transducers, power supplies, rotational elements, computers, compressors, and/or other mechanisms or components that can position the imaging arm 105 (e.g., cause the imaging arm to raise, lower, move forward, move backward, move left, move right, rotate laterally clockwise, rotate laterally counterclockwise, rotate orbitally clockwise, rotate orbitally counterclockwise, and/or otherwise move in a desired direction). For example, feedback of the position of the imaging arm within a range of travel of the servo controller may be provided by the use of a moving icon on the video display 244 of the imaging system 100.

The control panel 120 can comprise one or more control mechanisms. The control mechanisms can include brightness contrast buttons 189 and 190 in FIG. 8 for controlling contrast/brightness of an X-ray image. The control panel 120 can also comprise a voltage/current control (e.g., KV/uA buttons 191 and 192 in FIG. 8) that allows a user to increase or decrease the default kV and uA settings, thereby controlling some of the fluoroscopic X-ray technique factors that are used to create an image. The control panel 120 can also comprise one or more rotate controls (e.g., rotate buttons 178 and 179 in FIG. 8) that allow an image to be rotated on one or more displays 244. The rotate control can allow a user to rotate the image on the display by any angle up to 360 degrees. The control panel 120 can also comprise one or more flip controls, which allow a user to flip an image about a horizontal axis (as shown by flip button 193) and/or vertical axis (as shown by flip button 194).

The control panel 120 can contain additional or alternate controls. For example, the control panel 120 can comprise a control that allows a user to save an image/video (e.g., save button 195 in FIG. 8), a swap control (e.g., swap button 196 in FIG. 8) that allows a user to exchange images between the left and right sides of the monitor, a negate control (e.g., negate button 197 in FIG. 8) that can allow a user to reverse the display of light and dark values in an image, an auto control (e.g., auto button 198 in FIG. 8) that allows the user to have the system automatically select the optimum contrast and brightness values for an image, a low dose control (e.g., low dose button 199) that can allow the user to reduce the amount of radiation dose delivered to the patient, a metal adjust (e.g., metal adjust button 200 in FIG. 8) that can allow the user to reduce the appearance of metal in an image, a magnification control (e.g., mag button 201 in FIG. 8) that can adjust the magnification of the X-ray image, an alarm reset control (e.g., alarm reset button 202 in FIG. 8) that can turn off audible alarms, a viewer control (e.g., viewer button 203 in FIG. 8) that can be used to display saved images on the workstation monitor, a zoom/pan control (e.g., zoom pan button 204 in FIG. 8) that allows the system to zoom in and/or pan across an X-ray image, cursor controls (e.g., cursor buttons 213 in FIG. 8) that allows the user to navigate through the user interface, an enter control (e.g., enter button 205 in FIG. 8) that can be used to select a button or control from the workstation user interface, and/or any other control that allows the X-ray system 100 to capture desired X-ray images.

The control panel 120 can be disposed in any location on the support arm 115. FIG. 4 shows some embodiments in which the control panel 120 is disposed on two support members (e.g., support members 116 and 118). FIG. 5 shows other embodiments in which the control panel 120 is disposed on a single member (e.g., support member 118). And while the control panel can be disposed in any suitable location along the length of a support member (e.g., near the support arm's first end 172, second end 175, or in between the two), FIG. 4 shows some embodiments in which the control panel 120 is disposed between the first 172 and second 175 ends of the support arm 115 (e.g., on the first support member 116).

The control panel 120 can have any suitable orientation with respect to the support arm 115. In one example, FIG. 4 shows the control panel 120 is right side up when the support arm 115 is in a standard position. And while a first control panel on the first support member 116 can be right side up when the support arm 115 is in the standard position, a second control panel on the second support member 118 can be upside down. Accordingly, if a user rotates the support arm laterally 180 degrees, the second control panel will be in an upright position.

In some configurations, the control panel 120 is rotatable so as to allow the control panel to maintain an upright orientation when the support arm 115 can be rotated laterally manually, automatically, and/or virtually. In one example, the control panel is connected to the support arm through the use of a swivel or pivoting joint (e.g., a lazy-Susan swivel). Accordingly, when the support arm is rotated laterally, the control panel can be caused to maintain an upright position. In another example, where the control panel comprises a touch-screen interface (or a conventional or novel electronic visual display that can detect the presence and location of a touch within the display area), the display or graphical user interface can be rotated (much like the auto-rotation of smart phone screens) to maintain the proper orientation. FIGS. 6 and 7 illustrate that where the control panel 120 comprises a touch-screen interface 220, the control panel can maintain a first orientation (e.g., an upright orientation as illustrated by the number 1) when the support arm 115 is rotated 180 degrees from the standard position shown in FIG. 6.

In some embodiments, the control panel 120 communicates with a processing system (e.g., on the support structure or elsewhere) to operate the various functions of the X-ray system 100. The X-ray system can comprise any suitable processing system, such as a computer, which optionally includes one or more peripheral devices, such as one or more displays, printers, image storage devices, keyboards, etc. The processing system (under the direction of the control panel 120) can control the operation of various components of the imaging system; provide an image processing function to transform, in near real-time, image data received from the X-ray detector for display, printing, and communicating with peripheral devices; and perform a variety of other functions. The processing system may also be configured to communicate with one or more local area networks to transfer data (e.g., image data) to locations that are remote from the imaging arm 105. The processing system can comprise any suitable computing device (such as a personal computer, a mainframe, a hand-held computer, a minicomputer, a supercomputer, a network computer, a processor-based consumer electronic device, or the like). In some configurations, the processing system comprises a personal computer running a Microsoft Windows, MacOS, DOS, Unix, or another computer operating system.

Figure 9:
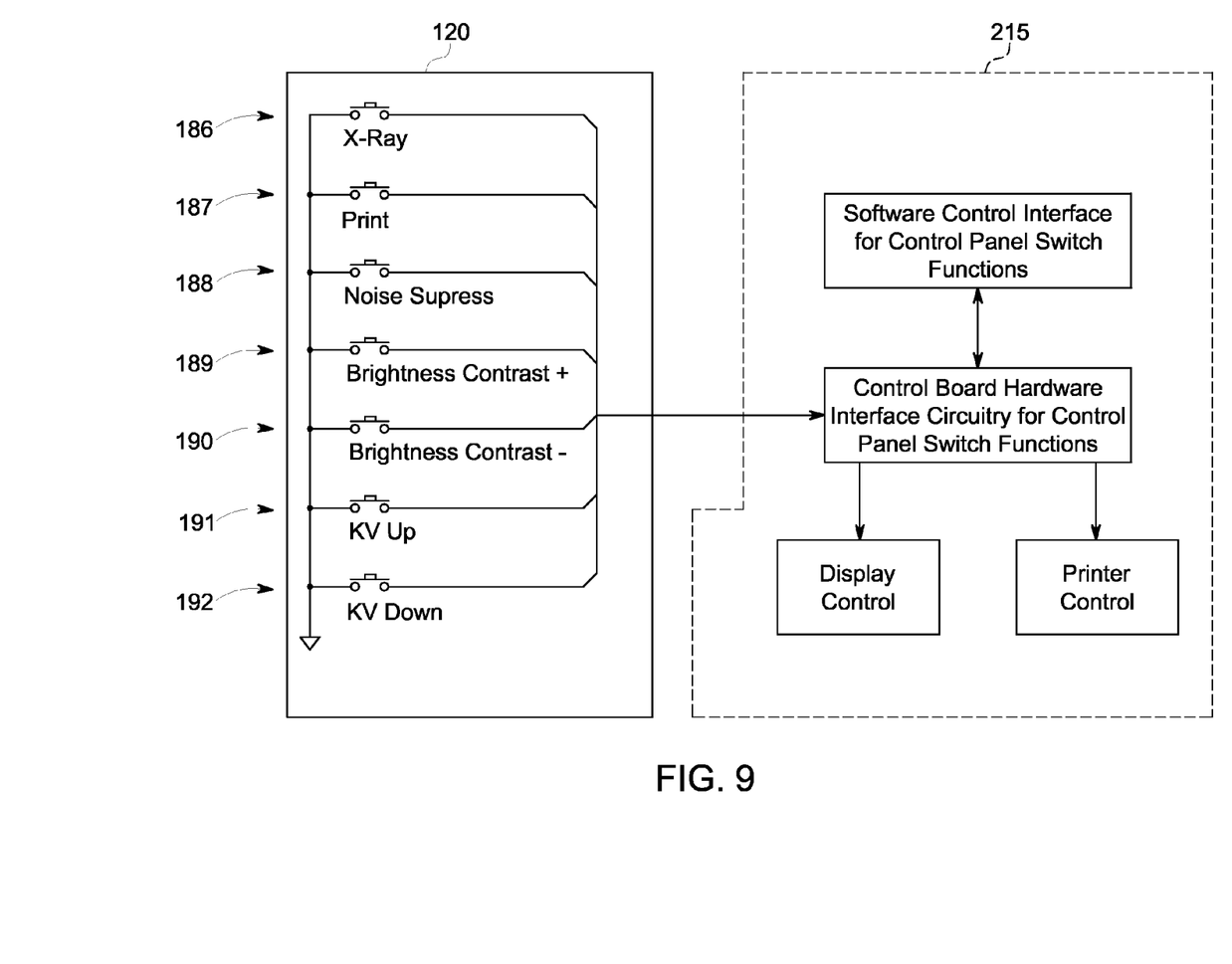
FIG. 9 shows a block diagram of some embodiments of the control panel with several switches and their interaction with a system computer.

The control panel 120 can be configured to receive power and/or transfer data (e.g., commands) to the processing system. In some embodiments, the control panel transfers data wirelessly (e.g., the control panel comprises an internal power source or is otherwise powered so that it can send wireless [e.g., Wi-Fi, Bluetooth, near-field communication, radio, microwave, infrared, etc.] signals to the processing system). In other embodiments, however, the control panel is connected to the imaging arm 105 through one or more cables that can enter the imaging arm in any suitable location. FIG. 8 shows some embodiments in which a cable 210 connects the control panel 120 to the imaging arm 105 through the orbital pivot joint 110 (e.g., by being threaded through (or near) the orbital pivot joint and/or by being electrically connected to the imaging arm via a slip ring disposed at the orbital pivot joint). FIG. 9 illustrates a block diagram showing some embodiments of the electrical connections between the control panel 120 and a system computer 215.

The support arm 115 and control panel 120 (and hence the imaging arm 105) can be physically connected to any support structure capable of holding the imaging arm at a desired vertical and/or horizontal position. In some configurations, the support arm and control panel are physically connected (e.g., via an articulating arm 240, a gantry, etc.) to a fixed support structure, such as a wall, a column, a floor, a shelf, a cabinet, a stationary frame, a ceiling, a door, a sliding structure, a bed, a gurney, a rail, and/or any other support structure that is not intended to be easily moved and repositioned around a patient.

In other configurations, though, the support arm 115 and control panel 120 (and hence the imaging arm 105) are physically connected to a movable support structure (e.g., the movable base assembly 230). In such configurations, the movable support structure can be configured to move across a floor while supporting the support arm and at least some other components of the X-ray system 100. Thus, the movable support structure can comprise one or more wheels, shelves, handles, monitors, computers, stabilizing members, limbs, legs, struts, cables, and/or weights (to prevent the weight of the imaging arm and/or any other component from tipping the movable support structure). FIG. 1 shows some embodiments in which the movable support structure 230 comprises a wheeled structure 235 that supports the support arm 115, control panel 120, and imaging arm 105 (e.g., via an arm assembly 240 or other support assembly).

Figure 10:
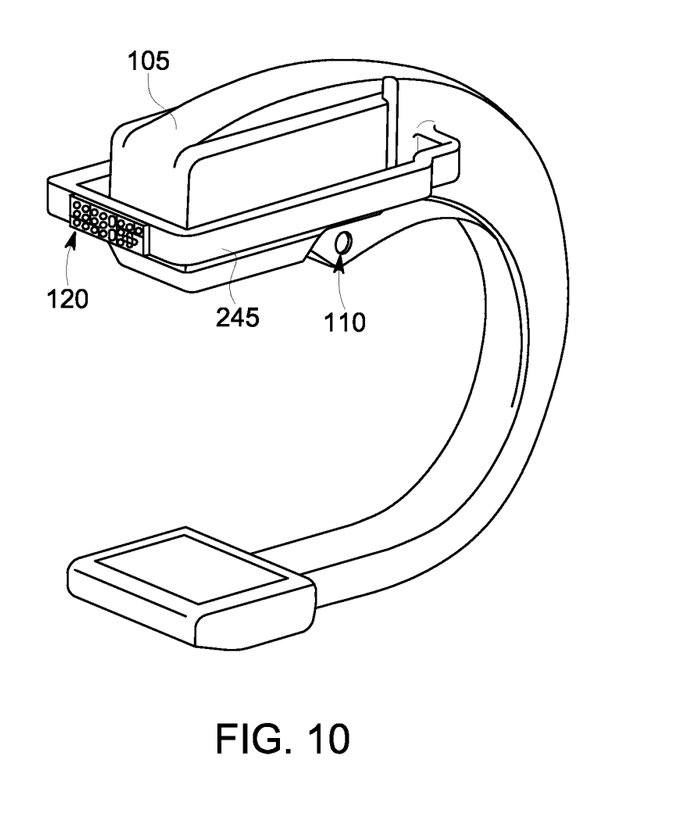
FIG. 10 shows a perspective view of some embodiments of the X-ray imaging arm with a control panel disposed proximate a handle of the imaging arm.

The described systems and methods can be modified in any suitable manner that allows the control panel 120 to be disposed on the support arm 115 and that otherwise allows the X-ray system 100 to operate. In one example, the system comprises a connection mechanism that allows the control panel to be selectively connected to and removed from the support arm 115. In this example, the control panel can communicate with the X-ray system wirelessly or through one or more wires that allow the control panel to be moved from the support arm while still allowing the control panel to communicate with the processing system (e.g., computer 215). Accordingly, where the control panel is corded or cordless, a user can use the control panel to operate the system when the user is separated from the support arm. The control panel 120 can be located on or near the imaging arm 105, a handle connected to the imaging arm, the moveable base assembly 230, or the arm assembly 240. FIG. 10 shows some configurations in which the control panel 120 is disposed on a handle 245 which is attached to the imaging arm 105 near the X-ray source 135. In other configurations, the handle (and control panel 120 attached thereto) can be attached to the imaging arm at any other location that allows a user to move the imaging arm by moving the handle.

The systems and methods for controlling an X-ray imaging system can be used for any X-ray imaging process. By way of example, an operator can stand near the support arm 115 and can orbitally rotate the X-ray imaging arm 105 while the control panel 120 substantially maintains its location and orientation.

The systems and methods described above have several useful features. First, where the control panel 120 is placed on the support arm 115, the control panel 120 can be in a convenient location that easily allows it to be accessed and used by a user. Second, because the control panel can be disposed on the support arm, as opposed to the mini C-arm 130, the control panel can remain in substantially the same position when the C-arm is rotated. Third, where the control panel is disposed on the support arm, a user can control the X-ray system while maintaining the user's hands outside of the X-ray beam. Fourth, by placing the control panel on the support arm, a user in close proximity to the imaging arm (e.g., a person in a sterile zone of an operating room) can use and control the arm without being forced to move away from the machine or to have another person in a remote location use the machine. Fifth, where the control panel is disposed on a handle that is attached to the imaging arm, the control panel may remain in a convenient location as a user uses the handle to move the imaging arm.

In addition to any previously indicated modification, numerous other variations and alternative arrangements may be devised by those skilled in the art without departing from the spirit and scope of this description, and appended claims are intended to cover such modifications and arrangements. Thus, while the information has been described above with particularity and detail in connection with what is presently deemed to be the most practical and preferred aspects, it will be apparent to those of ordinary skill in the art that numerous modifications, including, but not limited to, form, function, manner of operation and use may be made without departing from the principles and concepts set forth herein. Also, as used herein, the examples and embodiments, in all respects, are meant to be illustrative only and should not be construed to be limiting in any manner.

The invention claimed is:

1. A mobile X-ray imaging system, comprising:
    a moveable base assembly;
    an articulating arm assembly coupled to the moveable base assembly;
    a support arm assembly having a first end coupled to the articulating arm assembly; and
    an X-ray imaging arm having an X-ray source and an X-ray detector disposed at nearly opposing locations on the X-ray imaging arm, and coupled to a second end of the support arm assembly at an orbital pivot joint;
    wherein the support arm assembly includes at least one X-ray control panel disposed thereon and configured to control operation of the moveable X-ray imaging system.

2. The mobile X-ray imaging system of claim 1, wherein the first end of the support arm assembly rotationally connects to the articulating arm assembly to provide the support arm assembly with an axis of lateral rotation, and wherein the at least one X-ray control panel is capable of retaining an orientation when the support arm assembly is rotated laterally.

3. The mobile X-ray imaging system of claim 1, wherein the at least one X-ray control panel comprises a plurality of push button switches.

4. The mobile X-ray imaging system of claim 1, wherein the at least one X-ray control panel comprises a touch-screen interface.

* * * * *